(12) United States Patent
Albright et al.

(10) Patent No.: US 10,533,982 B2
(45) Date of Patent: *Jan. 14, 2020

(54) MASS FLOW CONTROLLER AND METHOD FOR CONTROLLING A MASS FLOW RATE OF A GAS IN A GAS STREAM

(71) Applicant: Hitachi Metals, Ltd., Minato-ku, Tokyo (JP)

(72) Inventors: Patrick Albright, Wellington, CO (US); Ryan Johnson, Fort Collins, CO (US); Alexei V. Smirnov, Fort Collins, CO (US)

(73) Assignee: HITACHI METALS, LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/412,996

(22) Filed: May 15, 2019

(65) Prior Publication Data

US 2019/0265218 A1      Aug. 29, 2019

Related U.S. Application Data

(63) Continuation of application No. 15/378,810, filed on Dec. 14, 2016, now Pat. No. 10,295,518.

(60) Provisional application No. 62/266,832, filed on Dec. 14, 2015.

(51) Int. Cl.
| | | |
|---|---|---|
| *G01N 33/00* | (2006.01) | |
| *G01F 1/68* | (2006.01) | |
| *G01N 25/00* | (2006.01) | |
| *G01F 1/684* | (2006.01) | |
| *G01F 1/76* | (2006.01) | |
| *G01F 1/69* | (2006.01) | |
| *G01F 1/696* | (2006.01) | |
| *G01F 15/00* | (2006.01) | |

(52) U.S. Cl.
CPC ....... *G01N 33/0073* (2013.01); *G01F 1/6842* (2013.01); *G01F 1/69* (2013.01); *G01F 1/696* (2013.01); *G01F 1/76* (2013.01); *G01F 15/005* (2013.01); *G01N 25/00* (2013.01)

(58) Field of Classification Search
None
See application file for complete search history.

(56) References Cited

U.S. PATENT DOCUMENTS

| | | |
|---|---|---|
| 7,651,263 B2 | 1/2010 | Zolock et al. |
| 8,499,786 B2 | 8/2013 | Zolock et al. |
| 8,504,311 B2 | 8/2013 | Smirnov et al. |
| 8,800,589 B2 | 8/2014 | Minami et al. |
| 10,295,518 B2 * | 5/2019 | Albright ............ G01N 33/0073 |
| 2011/0247390 A1 | 10/2011 | Smirnov et al. |

(Continued)

*Primary Examiner* — Harshad R Patel
(74) *Attorney, Agent, or Firm* — Neugeboren O'Dowd PC

(57) ABSTRACT

Systems and method for detecting a concentration of a gas in a gas stream are disclosed. A method includes receiving a gas stream including a carrier gas and a processing gas. Bridge signals of a mass flow sensor are used to produce a processing-gas concentration signal and a gas-stream mass flow rate signal. The gas stream is controlled so a mass flow rate of the processing gas equals a processing-gas-setpoint signal. In some variations, the processing-gas-concentration signal is produced using an upstream temperature of the gas stream and a bridge-derived temperature.

9 Claims, 9 Drawing Sheets

(56) References Cited

U.S. PATENT DOCUMENTS

2011/0247696 A1 10/2011 Zolock et al.
2014/0299206 A1 10/2014 Nagase et al.

\* cited by examiner

MASS FLOW CONTROLLER AND METHOD FOR CONTROLLING A MASS FLOW RATE OF A GAS IN A GAS STREAM

CLAIM OF PRIORITY UNDER 35 U.S.C. § 120

The present Application for Patent is a Continuation of patent application Ser. No. 15/378,810 entitled "SYSTEM AND METHOD FOR DETECTING CONCENTRATION OF A GAS IN A GAS STREAM" filed Dec. 14, 2016, pending, and assigned to the assignee hereof and hereby expressly incorporated by reference herein, which claims priority to Provisional Application No. 62/266,832 entitled "SYSTEM AND METHOD FOR DETECTING CONCENTRATION OF A GAS IN A GAS STREAM" filed Dec. 14, 2015, and assigned to the assignee hereof and hereby expressly incorporated by reference herein.

FIELD OF THE INVENTION

The present invention relates to systems and methods for mass flow measurement and control. In particular, but not by way of limitation, the present invention relates to systems and methods for measuring a concentration of a gas species in a flow of gas and control based upon the same.

BACKGROUND OF THE INVENTION

Several different types of processing operations (e.g., thin film deposition operations) rely on a precise delivery of a gas to a processing environment (e.g., a plasma processing environment). As the dimensions of the structures that are fabricated continue to diminish in size, the precision of the mass flow rate of the gas continues to increase in importance.

One approach to delivering a processing gas species to a process environment includes using a vaporizer to vaporize a source substance into a specific type of gas that is desired in the process environment. A pressurized carrier gas is then utilized to force the desired, processing gas to the process environment, but mixing the carrier gas with the processing gas results in two known gases in the gas stream, and problematically, the concentration of the processing gas is difficult to determine.

SUMMARY

According to an aspect, a mass flow controller includes a main flow path for a gas stream that includes a processing gas and a carrier gas. A temperature sensor is disposed and configured to obtain an upstream temperature of the gas stream and provide an upstream temperature signal indicative of the upstream temperature. A thermal mass flow sensor is coupled to the main flow path, and the thermal mass flow sensor is configured to provide a bridge-derived temperature signal indicative of a bridge-derived temperature and a gas-stream-flow-rate signal indicative of a mass flow rate of the gas stream. A gas concentration meter is disposed to receive the bridge-derived temperature signal, and the gas concentration meter is configured to provide a processing-gas-concentration signal based upon the bridge-derived temperature signal. A processing-gas mass flow meter is disposed to receive the processing-gas-concentration signal and the gas-stream-flow-rate signal, and the processing-gas mass flow meter is configured to provide a processing-gas-mass-flow-rate signal. A control valve is coupled to the conduit to control a mass flow rate of the gas stream, and a controller is disposed to receive the processing-gas-mass-flow-rate signal and adjust the control valve so the processing-gas-mass flow rate equals a processing-gas-setpoint signal.

According to another aspect, a mass flow control system includes a conduit to receive a gas stream including a carrier gas and a processing gas. A thermal mass flow sensor is disposed to receive the gas stream from the conduit and provide a bridge-derived temperature signal indicative of a bridge-derived temperature and a gas-stream-flow-rate signal. A gas concentration meter receives the bridge-derived temperature signal and the gas-stream-flow-rate signal and provides a processing-gas-concentration signal based upon the bridge-derived temperature signal and a gas-stream-flow-rate signal. A processing-gas mass flow meter is disposed to receive the processing-gas-concentration signal and the gas-stream-flow-rate signal, and the processing-gas mass flow meter provides a processing-gas-mass-flow-rate signal. A control valve is coupled to the conduit to control a mass flow rate of the gas stream, and a controller receives the processing-gas-mass-flow-rate signal and adjusts the control valve so the processing-gas-mass flow rate equals a processing-gas-setpoint signal.

DETAILED DESCRIPTION

Disclosed herein are systems and methods for metering a concentration of a processing-gas relative to a carrier gas in a gas stream. As described herein, the gas stream includes both the processing gas and the carrier gas, and it is known that the processing gas and carrier gas make up the composition of the gas stream. In many variations of the disclosed systems and methods, information about the mass flow rate of the gas stream and the concentration of the processing gas are used to control a mass flow rate of the processing gas. It is noted that, as used herein and in the appended claims, the singular forms "a", "an", and "the" include plural referents unless the context clearly dictates otherwise.

Figure 1:
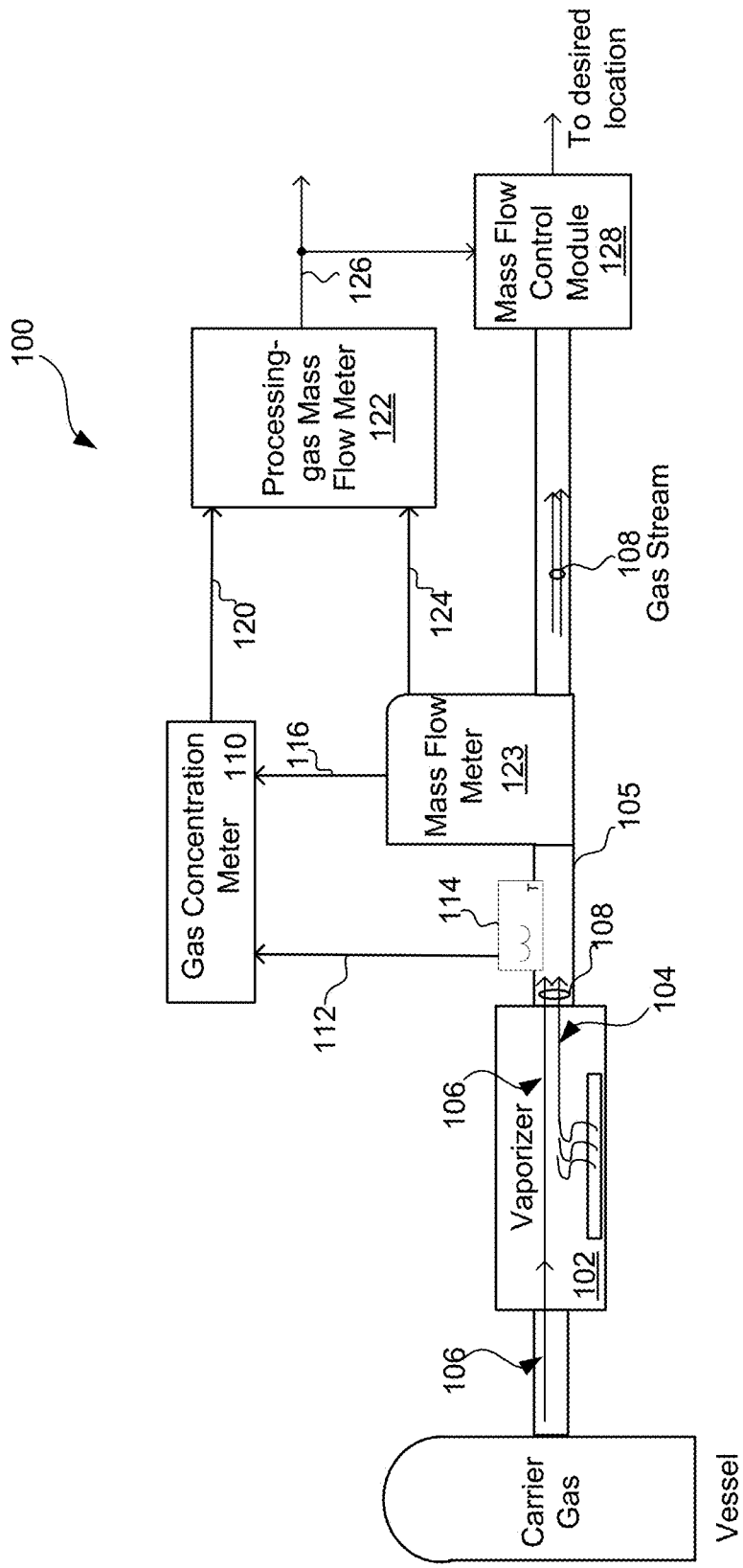
FIG. 1 is a block diagram depicting a mass flow control and gas concentration metering system.

Referring first to FIG. 1 shown is a mass flow control and gas concentration metering system 100. As shown, a vaporizer 102 is utilized to vaporize a material into a desired, processing gas 104, and a pressurized carrier gas 106 is employed to carry the processing gas 104 via conduit 105 in a desired direction. As shown, the carrier gas 106 mixes with the processing gas 104 to form a gas stream 108 that is provided to a desired location, such as for example, a plasma processing chamber (not shown). According to several aspects, a gas concentration meter 110 provides an indication of the concentration of the processing gas 104 in the gas stream 108. As a consequence, an operator of the process that utilizes the processing gas 104 may be provided with information about the concentration of the processing gas 104 in the gas stream 108.

As depicted, the gas concentration meter 110 receives an upstream temperature signal 112 from an upstream temperature sensor 114 and a bridge-derived temperature signal 116 from a mass flow meter 123. As described further herein, the upstream temperature signal 112 and the bridge-derived temperature signal 116 may be utilized by the gas concentration meter 110 to provide an indication of a concentration of the processing gas 104 in the gas stream 108. More specifically (as described in more detail further herein), a temperature-difference between an upstream temperature (conveyed by the upstream temperature signal 112) and a bridge-derived temperature (conveyed by the bridge-derived temperature signal 116) may be used to determine a concentration of the processing gas 104.

The gas concentration meter 110 may provide a processing-gas-concentration signal 120, which indicates a percentage of the mass flow of the gas stream 108 that is due to the processing gas 104. The processing-gas-concentration signal 120 may be reported to an operator of the system, and may be provided to a processing-gas mass flow meter 122.

As shown, the processing-gas mass flow meter 122 is disposed and configured to calculate a mass flow rate of the processing gas 104 using the processing-gas-concentration signal 120 and a gas-stream-mass-flow-rate signal 124. The gas-stream-mass-flow-rate signal 124 conveys a measure of the mass flow rate of the gas stream 108 (including the processing gas 104 and the carrier gas 106) as a whole. As an output, the processing-gas mass flow meter 122 provides a processing-gas-mass-flow-rate signal 126. As a consequence, an operator of the process that utilizes the processing gas 104 may be provided with information about the mass flow rate of the processing gas 104, and in some embodiments, the information about the mass flow rate of the processing gas 104 may optionally be utilized to control the flow rate of the gas stream 108 using a mass flow control module 128.

The depicted arrangement of components of the gas concentration metering system is intended to convey functional aspects of the system, but the system may be realized in many different forms without departing from the scope of the invention. For example, the vaporizer 102 and all the depicted components downstream of the vaporizer 102 may be integrated into a unitary vaporizer unit that is configured to enable an operator to control and deliver a precise amount of the processing gas 104. As another example, all of the components downstream from the vaporizer 102 may be implemented as part of a mass flow controller that is separate from the vaporizer 102.

Figure 2:
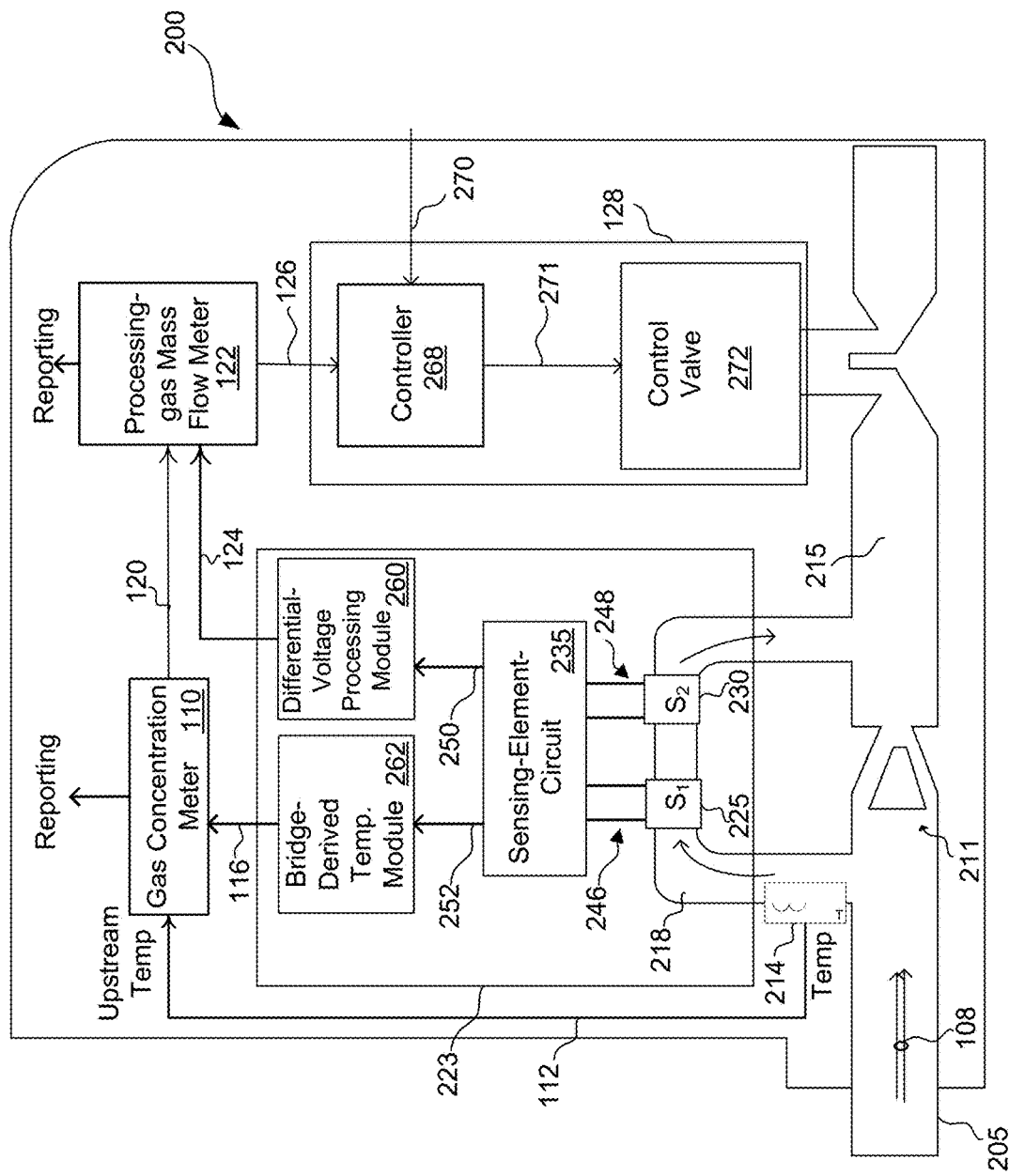
FIG. 2 is a block diagram depicting a mass flow controller that may be used to implement aspects of the system depicted in FIG. 1.

Referring next to FIG. 2, for example, shown is a functional block diagram of a mass flow controller (MFC) 200 in accordance with an illustrative embodiment of the invention. The illustrated arrangement of these components is logical and not meant to be an actual hardware diagram. Thus, the components can be combined, further separated, deleted and/or supplemented in an actual implementation.

As depicted, in the present embodiment a base of the MFC 200 is coupled to conduit 205, and a flow path of the MFC 200 for the gas stream 108 includes bypass portion 211 through which a gas flows. The bypass portion 211 directs a constant proportion of the gas stream 108 through a main path 215 and sensor tube 218. As a consequence, the flow rate of the gas stream 108 through the sensor tube 218 is indicative of the flow rate of the gas stream 108 flowing through the main path 215 of the MFC 200.

In this embodiment, the sensor tube 218 is a small bore tube that is part of a thermal mass flow sensor 223 of the MFC 100. And as shown, sensing elements 225 and 230 are coupled to (e.g., wound around) the outside of sensor tube 218. In one illustrative embodiment, sensing elements 225 and 230 are resistance-thermometer elements (e.g., coils of conductive wire), but other types of sensors (e.g., resistance temperature detectors (RTD and thermocouples) may also be utilized.

As depicted, sensing elements 225 and 230 are electrically connected to a sensing-element circuit 235. In general, the sensing-element circuit 235 is configured (responsive to signals 246, 248 from the sensing elements 225, 230) to provide a differential voltage 250 and a top voltage 252. Although in some variations both of the differential voltage 250 and the top voltage 252 may be used to measure the mass flow rate through the sensor tube 218, in the present embodiment, the differential voltage 250 is indicative of a mass flow rate of the gas stream 108 (comprising the carrier gas 106 and the processing gas 104) flowing through the main path 215 of the MFC 200, and the top voltage 252 is utilized by a bridge-derived temperature module 262 to generate the bridge-derived temperature signal 116.

As discussed with reference to FIG. 3 further herein, the sensing-element circuit 235 may be realized by a bridge circuit, and as disclosed by U.S. Pat. No. 7,651,263, entitled Method and Apparatus for Measuring the Temperature of a Gas in a Mass Flow Controller, which is incorporated herein by reference, the bridge-derived temperature module 262 may generate the bridge-derived temperature signal 116 utilizing the bridge circuit.

Also shown in FIG. 2 are an upstream temperature sensor 214 coupled to the sensor tube 218. As shown, the upstream temperature sensor 214 provides an upstream temperature signal 212 to the gas concentration meter 110, which generates the processing-gas-concentration signal 120 based upon the upstream temperature signal 212 and the bridge-derived temperature signal 116. Although the processing-gas concentration signal 120 may be represented in a variety of forms, it is contemplated that the processing-gas concentration signal 120 may be representative of a percentage of mass flow in the gas stream 108 that is made up of the processing gas 104.

As shown in FIG. 2, the differential voltage 250 may be processed by a differential-voltage processing module 260 to generate a gas-stream-flow-rate signal 124 representative of the mass flow rate of the gas stream 108 (that includes the carrier gas 106 and the processing gas 104). For example, the differential-voltage processing module 260 may amplify and convert, using an analog to digital converter, the differential voltage 250 to a digital representation of the differential voltage 250. And as one of ordinary skill in the art will readily recognize, the differential-voltage processing module 260 may also adjust the differential voltage 250 (e.g., by adjusting predetermined calibration coefficients) based upon physical characteristics of the MFC 200.

The processing-gas mass flow meter 122 generally operates to provide a processing-gas-mass-flow-rate signal 126 as an indication of the mass flow rate of the processing gas 104 utilizing the mass flow rate of the gas stream 108 and the concentration of the processing gas 104 in the gas stream. As shown, a mass flow rate of the processing gas 104 may be reported to an operator of the system, and the processing-gas-mass-flow-rate signal 126 may also be utilized to control a mass flow rate of the processing gas 104. More specifically, a controller 268 may generate a control signal 271 for a control valve 272 based upon a difference between a processing-gas-setpoint signal 270 and the processing-gas mass flow rate (represented by the processing-gas-mass-flow-rate signal 126).

Figure 3:
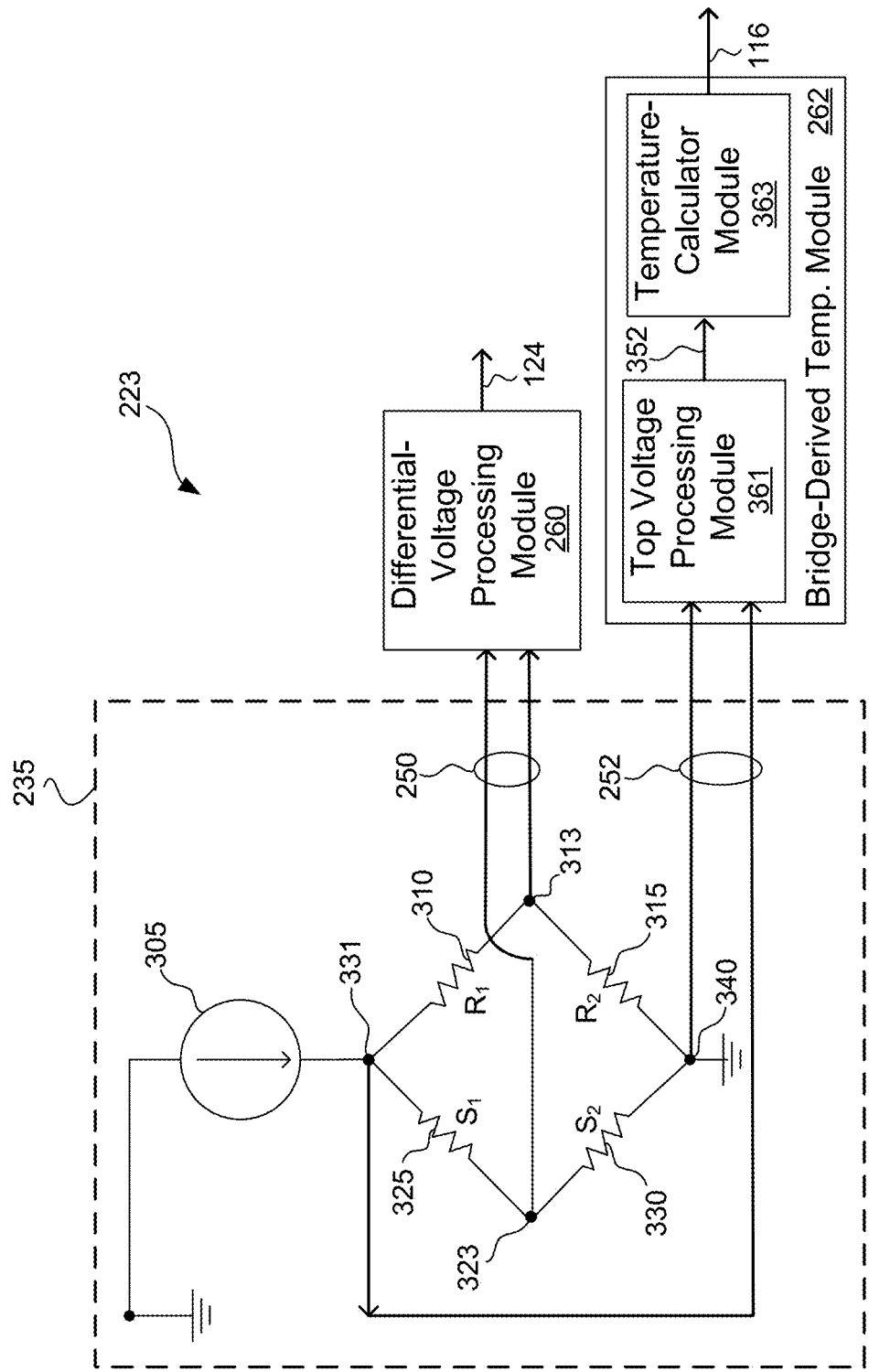
FIG. 3 is an exemplary thermal mass flow sensor and sensing-element circuit that may be used to implement aspects of FIG. 2.

Referring next to FIG. 3, it is a diagram depicting details of the thermal mass flow sensor 223, and in particular, details of the sensing-element circuit 235. As shown, a current source 305 supplies a substantially constant electrical current to a bridge circuit, which includes four nodes (331, 313, 340, and 323) between which elements are connected.

Among those elements are two fixed resistive elements 310 and 315 (R1 and R2, respectively). In one illustrative embodiment, fixed resistive elements 310 and 315 are both 10 k Ohm precision resistors. Resistances 325 and 330 (S1 and S2), which form a leg of the bridge circuit in this embodiment, are temperature-dependent resistances (e.g., coils) that correspond to sensing elements 225 and 230, respectively. Those skilled in the art will notice that sensing elements 325 and 330 have one node, node 323, in common.

The current source 305 in this embodiment supplies sensing elements 325 and 330 with a substantially constant electrical current, resulting in the heating of sensor tube 218. The gas flow produces a temperature differential, which produces the differential voltage 250 between a second node 313 and a fourth node 323, and the top voltage 252 between a first node 331 and a third node 340 changes because the average temperature of the sensors is decreasing due to gas flow.

The differential voltage 250 varies with the temperature differential between sensing elements 325 and 330 in an approximately proportional manner, and top voltage 252 varies, in a nonlinear manner, based upon average temperature. As depicted, the differential voltage 250 may be fed to the differential-voltage processing module 260 to be processed (e.g., fed to a differential amplifier, digitized, calibrated, and normalized) so that the differential voltage 250 may be used to provide an indication of the mass flow rate of the gas stream.

As shown, the bridge-derived temperature module may include a top voltage processing module 361 and a temperature-calculator module 363. The top voltage processing module 361 is configured to digitize the top voltage 252 to provide a top voltage signal 352, which is a digital representation of the top voltage 252. The temperature calculator module 363 is configured to produce the bridge-derived temperature signal 116 by accounting for a component of the top voltage signal 352 that is dependent on the mass flow rate of the gas stream 108 flowing through the mass flow sensor 223. Details about how the temperature-calculator module 363 may utilize the top voltage signal 352 to generate the bridge-derived temperature signal 116 are disclosed in U.S. Pat. No. 7,651,263, which is incorporated by reference.

Referring again to FIG. 1, the gas concentration meters 110, may utilize a formula or may use a lookup table when generating the gas-concentration signal 120. As briefly discussed above, the temperature-difference between the upstream temperature and the bridge-derived temperature may be used to determine a concentration of the processing gas 104 in the gas stream 108 based upon a known relationship between the temperature-difference and the concentration of the processing gas 104 when carried by the carrier gas 106.

Figure 4:
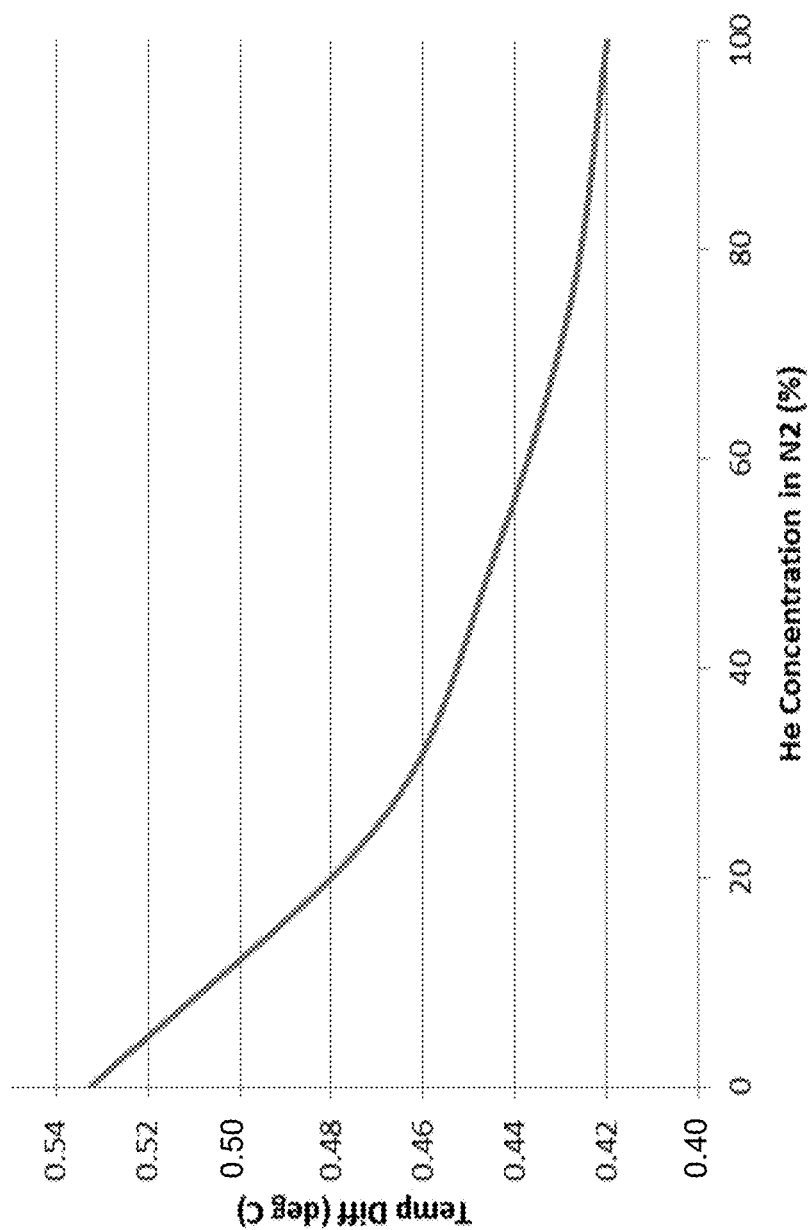
FIG. 4 is a graph depicting a relationship between a difference between the upstream temperature and bridge-derived temperature and a concentration of processing gas.

Referring to FIG. 4 for example, shown is a graph depicting a relationship between the temperature-difference and a concentration of a particular processing gas (helium) when carried by a particular carrier gas (nitrogen). It should be recognized that these gases are merely exemplary. As shown, having temperature-difference enables a corresponding point in the graph (corresponding to a concentration value in terms of percent) to be identified. In this way, the temperature-difference may be utilized to obtain the concentration of the processing gas on an ongoing basis.

The gas concentration meter 110 may utilized stored data (mapping temperature-difference values to concentration percentages) or the gas concentration meter 110 may utilize an equation to calculate the concentration based upon the temperature-difference. As one of ordinary skill in the art will appreciate, data (such as the date depicted in FIG. 4) may be empirically obtained using precision instruments in a controlled environment where processing gas concentration levels may be precisely controlled. And an equation may be derived from the data that is obtained.

The information about the concentration of the processing gas 104 may simply be reported, and an alarm may be triggered if the concentration varies beyond a threshold. In other embodiments, the concentration of the processing gas may be used to control the mass flow of the gas stream 108 so that a mass flow rate of the processing gas 104 stays at a desired level (e.g., as set by the processing gas set point 270).

Figure 5:
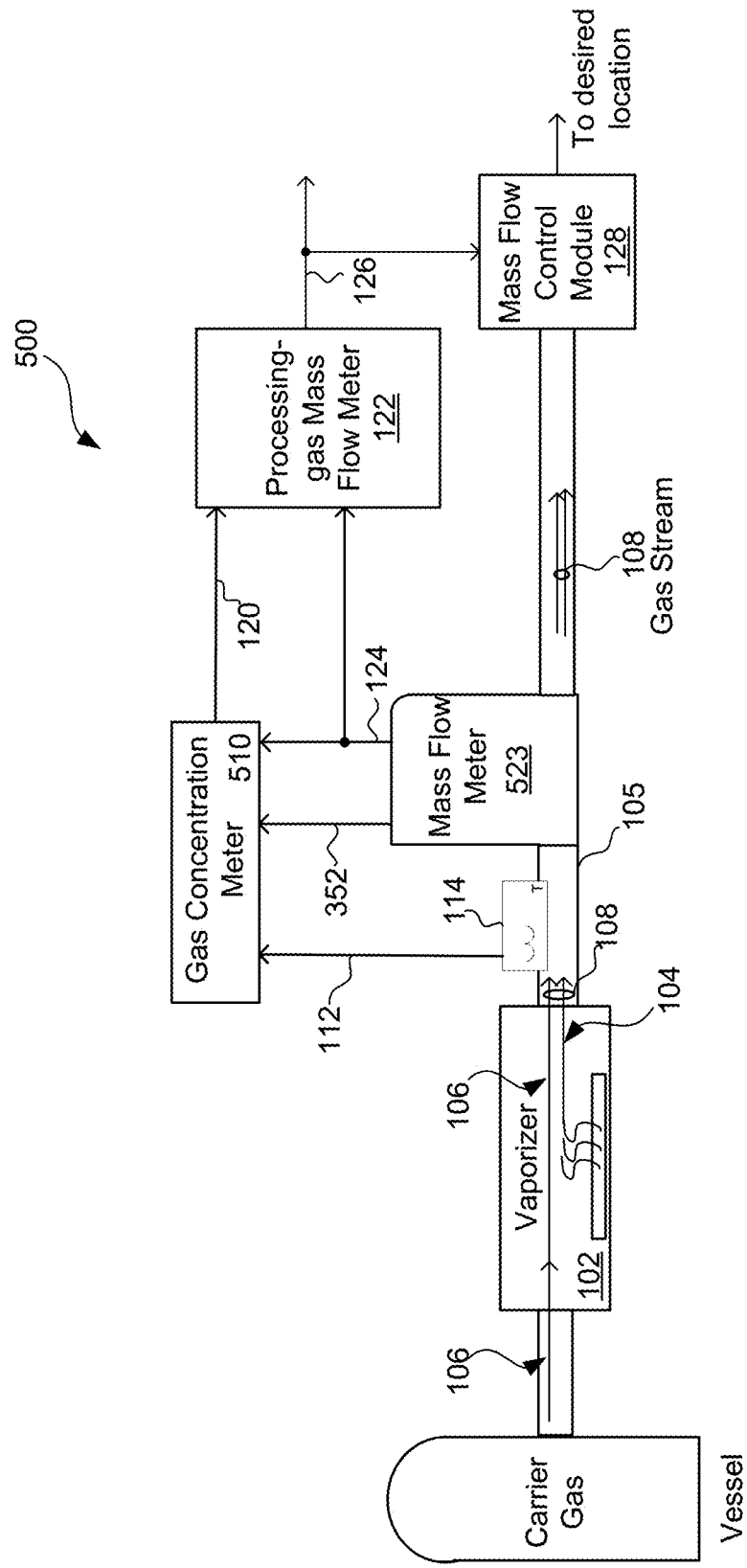
FIG. 5 is a block diagram depicting a mass flow control and gas concentration metering system.

Referring next to FIG. 5, shown is another embodiment of a mass flow control and gas concentration metering system 500. The mass flow control and gas concentration metering system 500 is similar to the embodiment depicted in FIG. 1 except a mass flow meter 523 is configured to provide a top voltage signal 352 and the gas-stream-flow-rate signal 124 to a gas concentration meter 510. The gas concentration meter 510 in this embodiment is configured to produce the processing-gas-concentration signal 120 using the top voltage signal 352 and the gas-stream-flow-rate signal 124 based upon i) a known relationship between the top voltage signal 352 and the gas-stream-flow-rate signal 124 relative to the processing gas 104; and ii) a known relationship between the top voltage signal 352 and the gas-stream-flow-rate signal 124 relative to the carrier gas 106.

Figure 6:
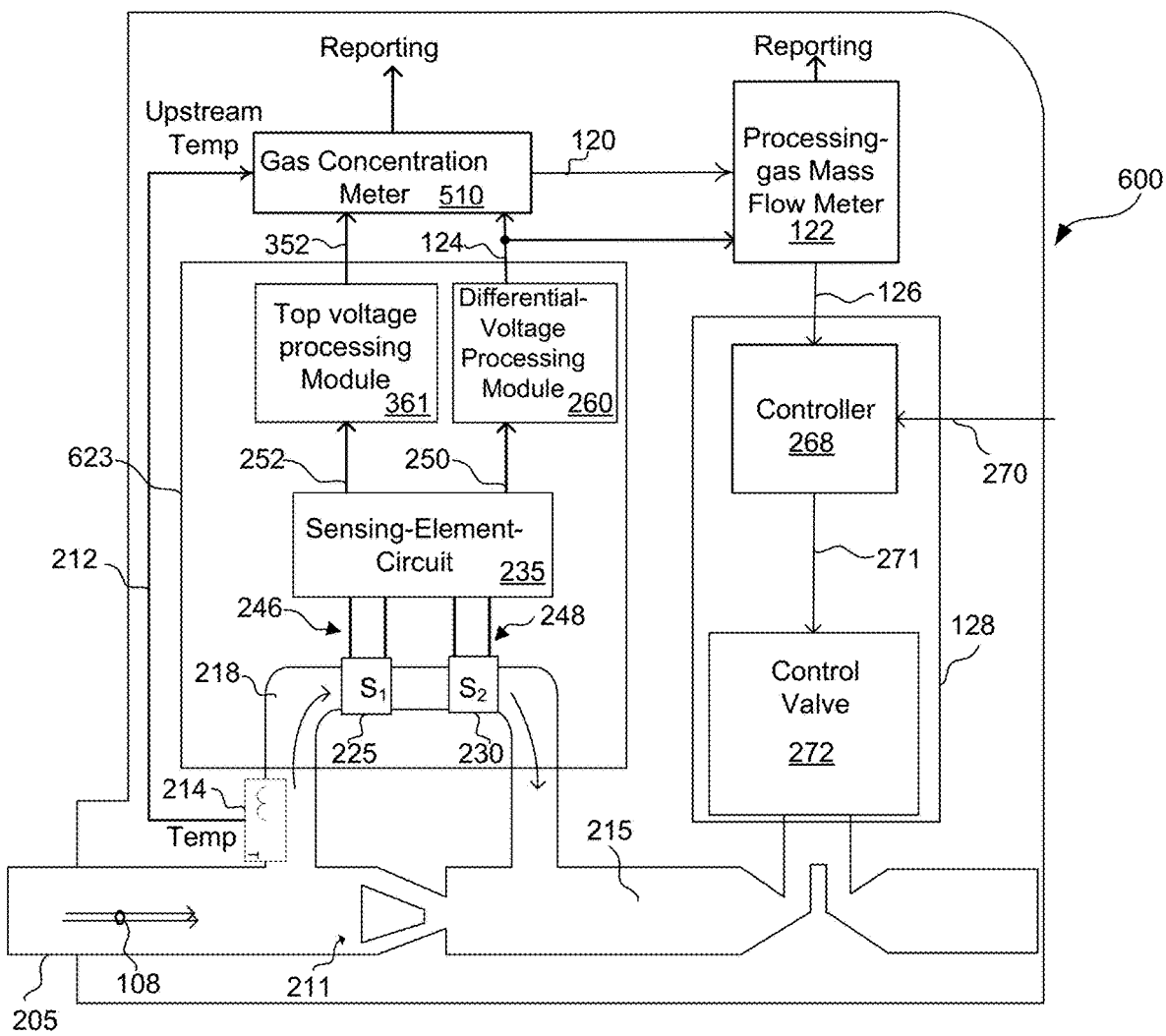
FIG. 6 is a block diagram depicting a mass flow controller that may be used to implement aspects of the system depicted in FIG. 5.

FIG. 6 depicts an exemplary mass flow controller 600 in which mass flow metering and control capability are integrated in the mass flow controller 600. The mass flow controller 600 is similar to the mass flow controller of FIG. 2, but the mass flow controller 600 differs in that a thermal mass flow sensor 623 in FIG. 6 does not include the bridge-derived temperature module 262. More specifically, the mass flow sensor 623 does not include the temperature calculator module 363 discussed with reference to FIG. 3. Instead, the top voltage processing module 361 provides the top voltage signal 352 directly to the gas concentration meter 510.

Figure 7:
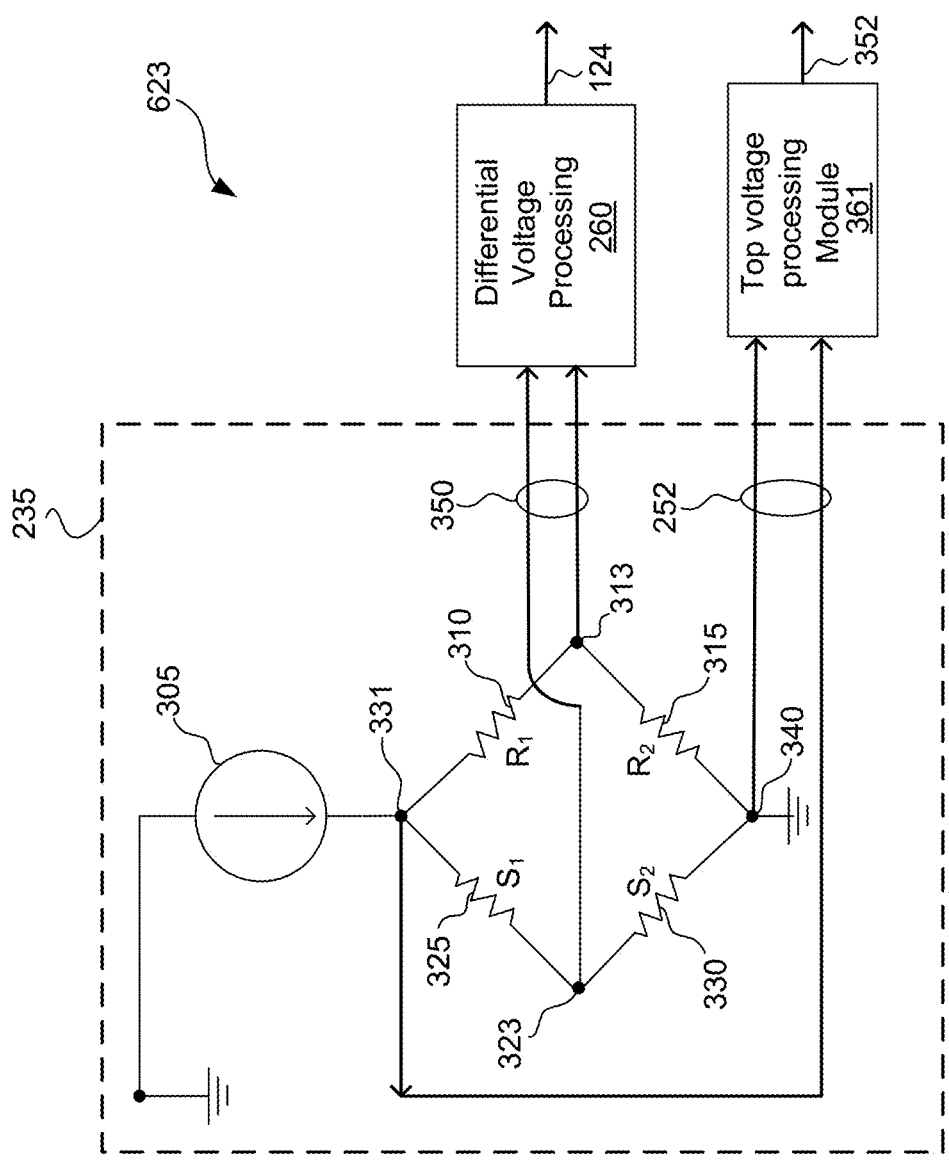
FIG. 7 is an exemplary thermal mass flow sensor and sensing-element circuit that may be used to implement aspects of FIG. 6.

Referring to FIG. 7, shown is a detailed view of the thermal mass flow sensor of FIG. 6. As shown, the thermal mass flow sensor 623 is similar to the thermal mass flow sensor 223 depicted in FIG. 3 except the thermal mass flow sensor 623 does not include the temperature calculator module 363, and instead provides the top voltage signal 352 as an output.

Figure 8:
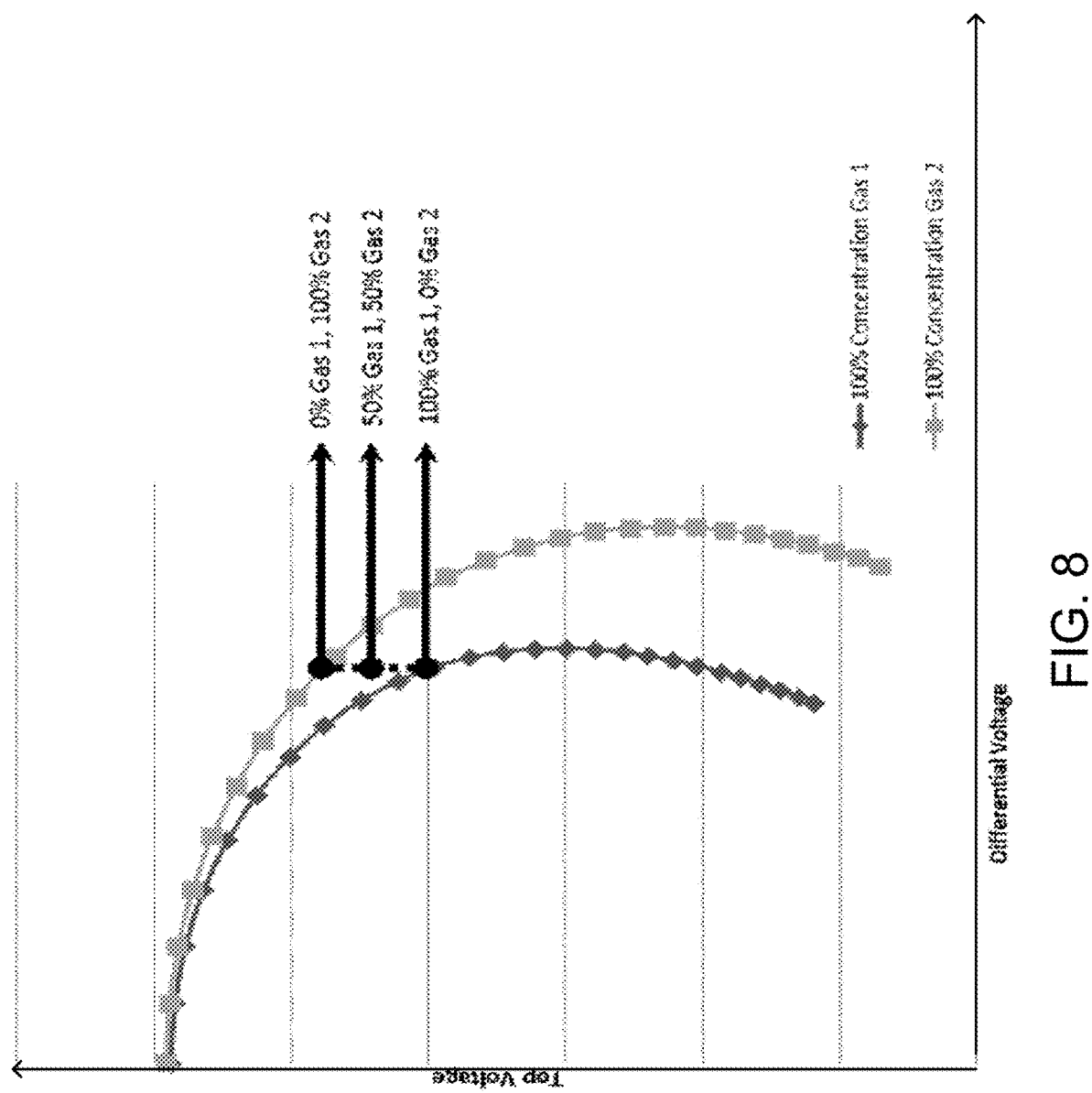
FIG. 8 is a graph depicting relationships between gas concentrations, a top voltage and a differential voltage.

Referring to FIG. 8, shown is a graph depicting two curves of top voltage versus differential voltage. Each of the curves corresponds to a different one of either the processing gas 104 or the carrier gas 106 in a 100% concentration. As shown, for a given differential voltage, there will be a specific top voltage. In the embodiment depicted in FIGS. 6 and 7, the gas-stream-flow-rate signal 124 represents the differential voltage and the top voltage signal 352 represents the top voltage.

As the concentration of the gases changes in the gas stream 108, for a given differential voltage, the top voltage will fall somewhere between the top voltages for the 100% concentration of either gas. The location of this top voltage is used to calculate the concentration of the gasses. The calculation can be performed by the gas concentration meter 510 using characteristic equations or lookup tables.

The top voltage provided by the top voltage processing module 361 may also be dependent upon the temperature of the gas stream 108. Therefore, the upstream temperature signal 212 may be used as an independent temperature measurement of the gas stream to normalize a relationship of the top voltage versus differential voltage.

As discussed, the gas concentration meters 110, 510 disclosed herein rely upon an awareness of the type of processing gas 104 and the type of carrier gas 106 that are in the gas stream 108. More specifically, the determination of the concentration of the processing gas 104 generally depends upon a specific known relationships between the differential voltage 250 and a top voltage 252 and relative concentrations of the processing gas 104 and the carrier gas 106 in the gas stream 108. In some implementations, the gas concentration meters 110, 510 may have gas-type-inputs so that the type of processing gas 104 and the type of carrier gas 106 may be provided to the gas concentration meters 110, 510. In this way, the gas concentration meters 110, 510 may select the appropriate equation and/or lookup table for the specific two-gas, processing-gas-carrier-gas combination in the gas stream 108.

Figure 9:
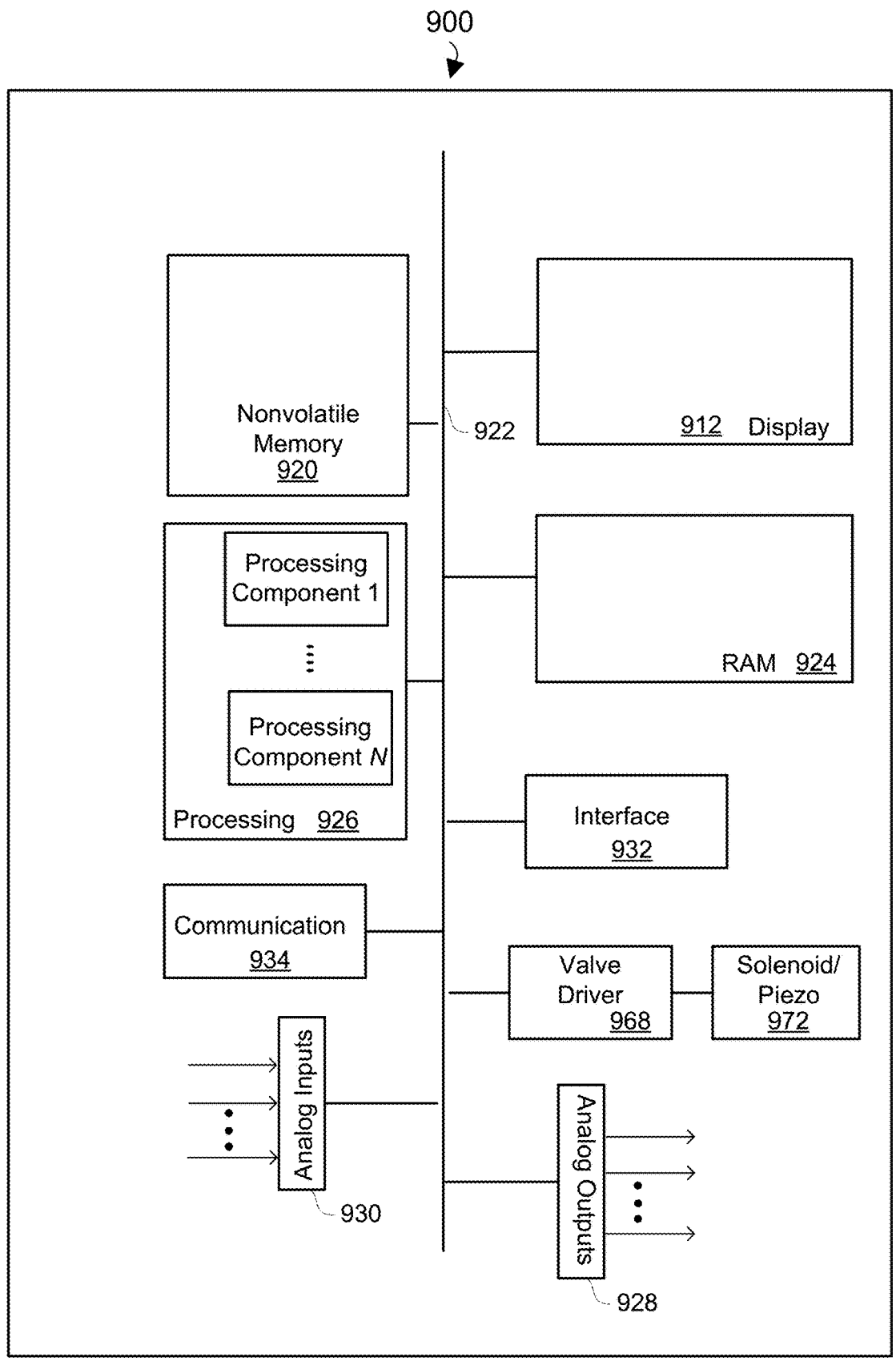
FIG. 9 is a block diagram depicting exemplary physical components that may be used to realize aspects described herein.

Referring next to FIG. 9, shown is a block diagram of a computing system 900 depicting physical components that may be utilized to realize aspects of the systems described herein. As shown, a display 912 and nonvolatile memory 920 are coupled to a bus 922 that is also coupled to random access memory ("RAM") 924, a processing portion (which includes N processing components) 926, a collection of analog outputs 928, and a collection of analog inputs 930. Although the components depicted in FIG. 9 represent physical components, it should be recognized that the depicted computing system may be replicated and distributed to implement aspects of the systems described herein.

The display 912 generally operates to provide a presentation of content (e.g., processing-gas-concentration) to a user, and in several implementations, the display 912 is realized by an LCD or OLED display. In general, the nonvolatile memory 920 functions to store (e.g., persistently store) data and executable code including non-transitory processor-executable code that is associated with functional components described herein. In some embodiments for example, the nonvolatile memory 920 includes bootloader code, software, operating system code, file system code, and code to facilitate the methods described herein.

In many implementations, the nonvolatile memory 920 is realized by flash memory (e.g., NAND or ONENAND™ memory), but it is certainly contemplated that other memory types may be utilized as well. Although it may be possible to execute the code from the nonvolatile memory 920, the executable code in the nonvolatile memory 920 is typically loaded into RAM 924 and executed by one or more of the N processing components in the processing portion 926.

The N processing components in connection with RAM 924 generally operate to execute the instructions stored in nonvolatile memory 920 to effectuate functional components described herein. For example, the gas concentration meters 110, 510, bridge-derived temperature module 262, the processing-gas flow meter 122, the controller 268 and other logical aspects of mass flow controllers and mass flow meters described herein may be realized by one or more of the N processing components in connection with non-transitory processor-readable code that is executed from RAM 924.

Also shown in FIG. 9 are a valve driver 968 and a solenoid/piezo 972. The solenoid/piezo 972 may be one of a solenoid or a piezo component that modulates a position of the control valve 272. In implementations where the solenoid/piezo 972 is a piezo component, the valve driver 968 provides (responsive to the control signal 271) a voltage signal to the piezo component. In implementations where the solenoid/piezo 972 is a solenoid, the valve driver 968 provides (responsive to the control signal 271) a current signal to the piezo component.

An interface component 932 generally represents one or more components that enable a user to interact with the systems described herein. The interface component 932, for example, may include a keypad, touch screen, and one or more analog or digital controls, and the interface component 932 may be used to translate an input from a user into the mass flow set point signal. And the communication component 934 generally enables one or more components of the systems to communicate with external networks and devices including external processing components (e.g., plasma processing components). One of ordinary skill in the art will appreciate that the communication component 934 may include components (e.g., that are integrated or distributed) to enable a variety of wireless (e.g., WiFi) and wired (e.g., Ethernet) communications.

In conclusion, the present invention provides, among other things, a system and method for reporting a concentration of a gas type in a gas stream that includes two gas types. In some embodiments, the information about the concentration of the gas type may be used to control a mass flow rate of the gas type. Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions fall within the scope and spirit of the disclosed invention as expressed in the claims.

What is claimed is:

1. A mass flow controller comprising:
    a main flow path for a gas stream, the gas stream including
        a processing gas and a carrier gas;
    a temperature sensor disposed and configured to obtain an
        upstream temperature of the gas stream and provide an
        upstream temperature signal indicative of the upstream
        temperature;
    a thermal mass flow sensor coupled to the main flow path,
        wherein the thermal mass flow sensor is configured to
        provide a bridge-derived temperature signal indicative of a bridge-derived temperature and a gas-stream-flow-rate signal indicative of a mass flow rate of the gas stream;

a gas concentration meter disposed to receive the bridge-derived temperature signal, and the gas concentration meter is configured to provide a processing-gas-concentration signal based upon the bridge-derived temperature signal;

a processing-gas mass flow meter disposed to receive the processing-gas-concentration signal and the gas-stream-flow-rate signal, wherein the processing-gas mass flow meter is configured to provide a processing-gas-mass-flow-rate signal;

a control valve coupled to the conduit to control a mass flow rate of the gas stream; and a controller disposed to receive the processing-gas-mass-flow-rate signal and adjust the control valve so the processing-gas-mass flow rate equals a processing-gas-setpoint signal.

2. The mass flow controller of claim 1, wherein the thermal mass flow sensor includes:

a sensor tube coupled to the main flow path;

at least two sensing elements coupled to the sensor tube, wherein the at least two sensor elements are arranged in a bridge circuit;

a bridge-derived temperature module configured generate the bridge-derived temperature signal; and a differential-voltage processing module configured to produce the gas-stream-flow-rate signal based upon a differential voltage of the bridge circuit.

3. The mass flow controller of claim 1, wherein the gas concentration meter is configured to:

obtain a temperature-difference between the upstream temperature of the gas stream and the bridge-derived temperature; and utilize the temperature-difference to lookup a concentration value for the processing gas.

4. The mass flow controller of claim 1, wherein the gas concentration meter is configured to:

obtain the temperature-difference between the upstream temperature of the gas stream and the bridge-derived temperature; and utilize the temperature-difference to calculate the concentration value for the processing gas.

5. A mass flow control system comprising:

a conduit to receive a gas stream including a carrier gas and a processing gas;

a thermal mass flow sensor disposed to receive the gas stream from the conduit, wherein the thermal mass flow sensor is configured to provide a bridge-derived temperature signal indicative of a bridge-derived temperature and a gas-stream-flow-rate signal;

a gas concentration meter disposed to receive the bridge-derived temperature signal and the gas-stream-flow-rate signal, and the gas concentration meter is configured to provide a processing-gas-concentration signal based upon the bridge-derived temperature signal and a gas-stream-flow-rate signal;

a processing-gas mass flow meter disposed to receive the processing-gas-concentration signal and the gas-stream-flow-rate signal, wherein the processing-gas mass flow meter is configured to provide a processing-gas-mass-flow-rate signal;

a control valve coupled to the conduit to control a mass flow rate of the gas stream; and a controller disposed to receive the processing-gas-mass-flow-rate signal and adjust the control valve so the processing-gas-mass flow rate equals a processing-gas-setpoint signal.

6. The mass flow control system of claim 5, wherein the thermal mass flow sensor includes:

a sensor tube coupled to the conduit;

at least two sensing elements coupled to the sensor tube, wherein the at least two sensor elements are arranged in a bridge circuit;

a top voltage processing module configured generate the bridge-derived temperature signal using a top voltage of the bridge;

a differential-voltage processing module configured to produce the gas-stream-flow-rate signal based upon a differential voltage of the bridge circuit.

7. The mass flow control system of claim 5, including:

a vaporizer including:

an input to receive the carrier gas;

a chamber to produce the processing-gas from a material source; and an output coupled to the conduit to provide the gas stream.

8. The mass flow control system of claim 5, wherein the gas concentration meter is configured to:

utilize the bridge-derived temperature signal and the gas-stream-flow-rate signal to lookup a concentration value for the processing gas.

9. The mass flow control system of claim 5, wherein the gas concentration meter is configured to:

utilize the bridge-derived temperature signal and the gas-stream-flow-rate signal to calculate the concentration value for the processing gas.

* * * * *